(12) United States Patent
Lang

(10) Patent No.: US 7,931,930 B2
(45) Date of Patent: Apr. 26, 2011

(54) DELIVERY OF ACTIVE AGENTS USING A CHOCOLATE VEHICLE

(75) Inventor: Kevin W. Lang, Lloyd Neck, NY (US)

(73) Assignee: Delavau LLC, Philadelphia, PA (US)

( * ) Notice: Subject to any disclaimer, the term of this patent is extended or adjusted under 35 U.S.C. 154(b) by 1103 days.

(21) Appl. No.: 11/561,294

(22) Filed: Nov. 17, 2006

(65) Prior Publication Data

US 2007/0269493 A1 Nov. 22, 2007

Related U.S. Application Data

(63) Continuation of application No. 11/437,371, filed on May 19, 2006, now Pat. No. 7,820,221.

(51) Int. Cl.
*A23C 17/00* (2006.01)
*A23L 1/30* (2006.01)
*A01N 59/06* (2006.01)

(52) U.S. Cl. ............ 426/583; 426/27; 426/73; 426/74; 424/687

(58) Field of Classification Search .................. None
See application file for complete search history.

(56) References Cited

U.S. PATENT DOCUMENTS

| | | |
|---|---|---|
| 3,456,050 A | 7/1969 | Rieckmann et al. |
| 4,581,381 A | 4/1986 | Morris et al. |
| 4,609,543 A | 9/1986 | Morris et al. |
| 4,749,575 A | 6/1988 | Rotman |
| 4,797,288 A | 1/1989 | Sharma et al. |
| 4,882,154 A | 11/1989 | Yang et al. |
| 4,937,076 A | 6/1990 | Lapidus |
| 4,963,372 A | 10/1990 | Zumbe |
| 5,505,982 A | 4/1996 | Krawczyk |
| 5,525,352 A | 6/1996 | Kontos et al. |
| 6,197,356 B1 | 3/2001 | Girsh |
| 6,241,997 B1 | 6/2001 | Kershman et al. |
| 6,340,471 B1 | 1/2002 | Kershman et al. |
| 6,391,356 B1 * | 5/2002 | Willcocks et al. ............ 426/306 |
| 6,391,373 B1 | 5/2002 | Kaiser et al. |
| 6,673,383 B2 | 1/2004 | Cain et al. |
| 2002/0025360 A1 | 2/2002 | Yang et al. |
| 2002/0034574 A1 * | 3/2002 | Prosise et al. ................ 426/560 |
| 2005/0025811 A1 * | 2/2005 | Levin et al. .................... 424/429 |

FOREIGN PATENT DOCUMENTS

| | | |
|---|---|---|
| EP | 0832567 | 12/2001 |
| GB | 2266217 | 10/1993 |
| WO | WO 99/21440 | 5/1999 |
| WO | WO 99/26490 | 6/1999 |
| WO | WO 9926491 A1 * | 6/1999 |
| WO | WO 2006/015154 | 2/2006 |
| WO | WO 2006/084087 | 8/2006 |

OTHER PUBLICATIONS

MacMillan et al., In Situ Small Angle X-ray Scattering (SAXS) Studies of Polymorphism with the Associated Crystallization of Cocoa Butter Fat Using Shearing conditions, Crystal growth & design 2002, vol. 2, No. 3, 221-226.*
"Regal SSW Calcium Fortified Chocolate," Product Specification, Oct. 1, 2003 (2 pages).
"Healthy Indulgence" advertisement, Copyright Date 2004.
"Dark Chocolate CoCoCal™ Balls," Product Specification, Oct. 28, 2003.
"Adora™ Calcium the Gourmet Way," Product Specification, Oct. 25, 2004, (2 pages).
"Sensible Sweets," Health and Wellness, Jun. 27, 2006, p. 42-46.
"MOObles Calcium Fortified Chocolate for Kids," Product Quotation, May 16, 2002.
"Chocolate Good for the Bones," Product Announcement, Apr. 1, 2002.
"Adora. (Candy Product Update)" Mar. 2002, (3 pages).
"MOOOve over to MOObles. (Food Biz Kids)," Dec. 1, 2002.
"Maximizing Your Calcium Absorption," Lifestyle Articles, Oct. 25, 2004, p. 1-2.
"Vitamin K, what is the role of Vitamin K in VIACTIV® Soft Calcium Chews?" Lifestyle Articles, Oct. 25, 2004, p. 1-2.
"Calcium Benefits," Lifestyle Articles, Oct. 25, 2004, p. 1-2.
Press Release, "Thompson Candy Company Includes Adora™ Calcium Fortified Chocolates" Jan. 1, 2002, (4 pages).
Press Release, "Thompson Candy Company Introduces Calcium Fortified All Natural Milk Chocolate MOObles," Apr. 15, 2002.
"MOObles™ Chocolate Balls," Product Literature, May 20, 2002.
"V-110 Calcium Fortified Dark Confectionery Flavored Coating," Product Specifications, Oct. 5, 2001.
"V-022 Calcium Fortified Milk Chocolate Flavored Coating," Product Specifications, Jul. 18, 2001.
"Adora Calcium Fortified Premium Chocolate Bars w/ 900 mgs Calcium per Bar," Product Quotation, May 16, 2002.
"Adora Calcium Fortified Premium Chocolate Bars w/ 900 mgs Calcium per Bar," Product Quotation, Jan. 19, 2001.
"Adora Calcium Fortified Premium Chocolate Bars w/ 900 mgs Calcium per Bar," Product Quotation Memo, Jan. 19, 2001.
"Adora Calcium Fortified Premium Chocolate Bars w/ 900 mgs Calcium per Bar," Product Quotation, Feb. 22, 2002.
"Adora Calcium Fortified Natural Chocolate Bars," Product Quotation, Nov. 12, 2001.
"Adora Calcium Fortified Premium Chocolate Bars w/ 900 mgs Calcium per Bar," Product Quotation, Apr. 30, 2002.
"Adora Calcium Fortified Premium Chocolate Bars w/ 900 mgs Calcium per Bar", Product Quotation, Mar. 1, 2002.
"Mineral Fortification of Dark Chocolate," Dec. 2006.
Shahkhalili et al., "Calcium Supplementation of Chocolate: Effect on Cocoa Butter Digestibility and Blood Lipids in Humans," Am. J. Clin. Nutr., 73:246-252, 2001.
*Delavau LLC v. Thompson Brands LLC*, Index No. 602160/06, Complaint filed on Jun. 20, 2006.
*Delavau LLC v. Thompson Brands LLC*, Index No. 602160/06, Answer filed on Jul. 21, 2006.
PCT Search Report dated May 2, 2008.

* cited by examiner

*Primary Examiner* — Michael G Hartley
*Assistant Examiner* — Nabila G Ebrahim
(74) *Attorney, Agent, or Firm* — Jonathan D. Ball; King & Spalding LLP

(57) ABSTRACT

This invention provides edible compositions comprising pharmaceutically or nutraceutically active agents in particulate form homogeneously dispersed in a fat matrix, such as chocolate or chocolate compound coating.

32 Claims, No Drawings

US 7,931,930 B2

DELIVERY OF ACTIVE AGENTS USING A CHOCOLATE VEHICLE

This application is a continuation application under 35 U.S.C. §120 of U.S. patent application Ser. No. 11/437,371, filed May 19, 2006, the entire contents of which are hereby incorporated by reference herein.

FIELD OF INVENTION

The present invention relates generally to compositions for oral consumption comprising one or more active agents. More particularly, the invention relates to the use of a fat matrix, such as chocolate, for delivering active agents.

BACKGROUND OF THE INVENTION

The continuing advances in medical and nutritional science have led to the development of a large number of pharmaceutical and nutraceutical agents which are prescribed or recommended for a variety of indications. In many cases, the efficacy of such agents in clinical settings is unquestioned. However, the established clinical efficacy of an agent is not always realized in the population at-large, owing in part to poor patient compliance.

For example, dietary calcium is an essential nutrient which has been established to play a vital role in building healthy teeth and bones, blood clotting, muscle contraction, and nerve function. In addition to these benefits, it has been suggested that calcium reduces the risk of recurrence of colon polyps. see Baron J. A. et al. *New England Journal of Medicine* 1999; 340: 101-107. Most notably, calcium reduces the risk of bone loss caused by osteoporosis in both men and women. Not surprisingly, physicians recommend calcium supplements more than any other dietary supplement.

Despite these advantages, it has been estimated that half of all Americans do not consume sufficient amounts of calcium. More troubling, 80% of women, the group at highest risk for developing osteoporosis, do not consume enough calcium.

This deficiency is due in part to the large daily intake of calcium that is suggested by physicians. The United States Recommended Daily Allowance ("USRDA") of calcium for adults is 800 to 1,400 mg. The National Academy of Sciences, Institute of Medicine recommends calcium intakes of 1,200 mg per day for people over 50 years of age and 1,300 mg per day for people under 19 years of age. In order to meet these recommendations, approximately 2.5 to 3.5 g of calcium carbonate, the must common source of dietary calcium, must be consumed daily to meet the recommendations. However, it is not practical to make tablets containing such large amounts of calcium carbonate. Consequently, supplemental calcium regimens typically comprise administering two tablets daily of 500 to 600 mg of calcium. Conventional calcium tablets are therefore very large and difficult or uncomfortable to swallow. This problem is exacerbated when excipients are also present in the formulation. As with any solid dose pharmaceutical or nutraceutical, large tablet size often leads to poor patient compliance. In addition to calcium supplements, this disadvantage is commonly encountered with tablets having large amounts of active ingredients, such as multi-vitamins and high-dose pharmaceuticals.

In other cases, poor patient compliance may result from the objectionable taste or consistency associated with certain active ingredients. For example, the active agent may be perceived as pasty, dry, dusty, chalky, bitter or may possess an unpleasant aftertaste. Vitamin B complex, for example, is particularly associated with unpleasant taste.

In view of these problems, there have been numerous attempts to deliver active agents in forms which are less objectionable to the consumer. One approach has been to formulate smaller tablets which are more comfortable to swallow. In this regard, special mention may be made of U.S. Patent Pub. No. US2005/0025811 to Levin et al. which discloses calcium carbonate tablets having volumes which are about 20 to about 35% smaller than conventional calcium carbonate tablets.

Other approaches have involved delivering active agents in the form of chewable confections. This approach has received considerable attention because size restraints are not as important as in other oral dosage forms and flavorants may therefore be added in sufficient quantities to mask unpleasant tastes characteristic of the active agent. For example, commercial chewable calcium supplements based on carbohydrate matrices are well known. There are nonetheless certain disadvantages associated with these products. Notably, carbohydrate matrices provide a hydrophilic environment which may promote microbial activity and consequently reduce shelf-life or require the presence of antimicrobial agents in the formulation.

There is a continuing need in the art for oral dosage forms for delivering active agents. It is therefore an object of the present invention to provide comestible compositions comprising active agents which present desirable organoleptic attributes (i.e., taste and texture) to the consumer. It is also an object of the present invention to provide comestible compositions comprising active agents which mask unpleasant tastes and textures associated with the active agents. It is further an object of the present invention to provide comestible compositions comprising active agents which are resistant to microbial activity.

SUMMARY OF THE INVENTION

In accordance with the foregoing objectives and others, the present invention provides compositions comprising chocolate or chocolate compound as a delivery vehicle for active agents. Chocolate is well-suited as a vehicle for delivering active agents in many respects. For example, the organoleptic characteristics of chocolate are excellent for masking unpleasant flavors associated with some active agents and imparting a smooth and creamy texture to compositions of active agents that are otherwise undesirably gritty. Chocolate is also a substantially anhydrous medium and is therefore resistant to microbial growth and to hydrolysis of water-sensitive active agents. Despite these advantages, chocolate has not found commercial acceptance as a pharmaceutical or nutraceutical delivery vehicle, owing in part to the difficulty of formulating chocolate compositions which comprise particulate active agents. It has surprisingly been found that chocolate dosage forms comprising pharmaceutically or nutraceutically effective amounts of particulate active agents may be formulated by carefully controlling the particle size of the particulate active agent.

In one aspect of the invention, compositions are provided which comprise (i) a particulate composition comprising one or more active agents, and (ii) a vehicle comprising a fat matrix. The particulate composition has a median particle diameter between about 1 µm (micron) and about 25 µm, preferably between about 10 µm and about 13 µm. The fat matrix has a melting point between about 30° C. and about 49° C. The particulate composition is typically homogeneously dispersed throughout the fat matrix.

In another aspect of the invention, a dietary supplement is provided comprising at least about 25% by weight calcium carbonate powder having a median particle size between about 1 µm and about 25 µm homogeneously dispersed throughout a fat matrix having a melting point between about 30° C. and about 49° C.

In a further aspect of the invention, an edible composition is provided comprising: (i) a particulate composition comprising one or more active agents, the particulate composition having a median particle diameter between about 10 µm and about 13 µm; and (ii) a vehicle comprising a fat matrix, the fat matrix having a melting point between about 30° C. and about 49° C.; wherein the particulate composition is dispersed homogeneously throughout the fat matrix. The particulate composition, which preferably includes calcium carbonate, may have a distribution of particle diameters wherein about 50% or more of the bulk volume of the particulate composition has a particle size between about ±66% of the median diameter and about 30% or more of the bulk volume has a particle size between about ±33% of the median diameter.

In yet another aspect of the invention, a dietary supplement is provided comprising a fat matrix having a melting point between about 30° C. and about 49° C.; wherein a 7 g serving of the dietary supplement comprises: (i) between about 1 and about 5,000 mg of calcium carbonate powder having a median particle diameter between about 1 µm and about 25 µm; (ii) one or more vitamins selected from the group consisting of: between 1 and about 35,000 IU (International Unit) of vitamin A; between 1 and about 1,000 mg of vitamin C; between 1 and about 4,000 IU of vitamin D; between 1 and about 450 IU of vitamin E; between 1 and about 250 mcg (microgram) of vitamin K; between 1 and about 15 mg of vitamin B-1 (thiamin); between 1 and about 17 mg of vitamin B-2 (riboflavin); between 1 and about 200 mg of vitamin B-3 (niacin); between 1 and about 100 mg of vitamin B-5 (pantothenic acid); between 1 and about 30 mg of vitamin B-6 (pyridoxine); between 1 and about 4,000 mcg of vitamin B-9 (folic acid); between 1 and about 250 mcg of vitamin B-12 (cobalamin); between 1 and about 1,000 mcg of vitamin H (biotin); or combinations thereof; and (iii) one or more minerals selected from the group consisting of: between 1 and about 180 mg of iron; between 1 and about 1,100 mg of phosphorous; between 1 and about 1,500 mcg of iodine; between 1 and about 4,000 mg of magnesium; between 1 and about 150 mg of zinc; between 1 and about 600 mcg of selenium; between 1 and about 20 mg of copper; between 1 and about 20 mg of manganese; between 1 and about 2,000 mcg of chromium; between 1 and about 750 mcg of molybdenum; or combinations thereof; wherein the calcium carbonate powder, vitamins, and minerals are homogeneously dispersed throughout the fat matrix.

In an additional aspect of the invention, a dietary supplement is provided comprising a chocolate or chocolate compound coating matrix having a melting point between about 35° C. and about 40° C. comprising one or more active agents selected from the group consisting of: vitamin A, vitamin C, vitamin D, vitamin E, vitamin K, thiamin, riboflavin, niacin, vitamin $B_6$, folic acid, vitamin $B_{12}$, biotin, pantothenic acid, calcium, phosphorus, iodine, magnesium, zinc, selenium, copper, manganese, chromium, molybdenum, chloride, potassium, boron, nickel, silicon, vanadium, lutein, lycopene, iron, tin, ginseng root, and ginkgo biloba leaf; wherein the one or more active agents are dispersed homogeneously throughout the chocolate or chocolate compound coating matrix and collectively comprise at least about 20% by weight of the chocolate or chocolate compound coating matrix; and wherein the apparent viscosity of the chocolate or chocolate compound coating matrix comprising the one or more active agents, in the molten state, is between about 500 and about 100,000 cP (centipoises) at 50° C. and a spindle rate of 20 RPM when measured on a spindle viscometer.

These and other aspects of the invention may be more clearly understood by reference to the following detailed description of the invention and the appended claims.

DETAILED DESCRIPTION OF THE INVENTION

In the following description of the invention, it is to be understood that the terms used have their ordinary and accustomed meanings in the art, unless otherwise specified. The term "active agent" is intended to broadly refer to any substance administered to an individual to achieve a biological effect. The term "active agent" includes, without limitation, pharmaceuticals, nutraceuticals, vitamins, minerals, herbal remedies, and the like.

The compositions of the invention comprise a fat matrix as a delivery vehicle for an active agent. In the broadest aspects of the invention, any fat is contemplated to be suitable, including but not limited to, saturated fats, mono-unsaturated fats, polyunsaturated fats, trans fats, and combinations thereof. Preferably, the fat is one which is solid at room temperature. In this regard, particular mention may be made of saturated fats comprising fatty acids having between 12 and 18 carbon atoms such as lauric, myristic, stearic, and palmitic acids, including, without limitation, vegetable shortening, butter, milk fat, coconut oil, palm oil, palm kernel oil, and hardened or hydrogenated vegetable oils. A particularly interesting fat is cocoa butter.

The skilled artisan will recognize that cocoa butter comprises varying amounts of palmitic-oleic-palmitic (POP), palmitic-oleic-stearic (POS), stearic-oleic-stearic (SOS), palmitic-oleic-oleic (POO), and stearic-oleic-oleic (SOO) triglycerides, depending on the country of origin. Cocoa butter is known to solidify into six polymorphic forms (often numbered as Forms I-VI), each of which comprises a fat matrix (i.e., a three-dimensional arrangement of fat molecules) that is substantially crystalline. Each of the forms has a different melting range, as shown in Table 1.

TABLE 1

| MELTING RANGES OF CRYSTALLINE FORMS OF COCOA BUTTER | |
|---|---|
| Polymorph | Melting Range (° C.) |
| I | 16-18 |
| II | 22-24 |
| III | 24-26 |
| IV | 26-28 |
| V | 32-34 |
| VI | 34-36 |

While each of the polymorphs is contemplated to be a useful variant of the invention, preferred embodiments will comprise cocoa butter in Form V. The Form V polymorph is solid at room temperature but advantageously melts below mouth temperature to provide a smooth mouthfeel and organoleptically pleasing experience when consumed.

In one embodiment, the fat matrix is provided by the cocoa butter in chocolate. Chocolate that is suitable for use in invention may be either a solid or liquid at room temperature, but typically will be a solid, and preferably will comprise the Form V polymorph of cocoa butter. However, the term "chocolate" is not limited to any particular polymorph and is not necessarily crystalline. Typically, cocoa butter comprises from about 5% to about 100% of the total fat of the chocolate. While many desirable chocolate products will have cocoa butter contents toward the upper end of this range, well known advances in chocolate technology have allowed substantial amounts of cocoa butter to be replaced by other fats, including, but not limited to, vegetable oils and the like, without sacrificing the organoleptic, textural, and mouthfeel properties of chocolate. With due regard to such advances in chocolate formulation, the compositions of the present invention, in the broadest sense, are not limited to any particular cocoa butter content. Nonetheless, certain desirable embodiments favor the use of substantial quantities of cocoa butter. Therefore, various embodiments of the invention presently contemplated to be useful include those having from about 10%, 15%, 20%, 25%, or 30% to about 70%, 75%, 80%, 85%, or 90% cocoa butter by weight of the total fat content. Exemplary embodiments have a cocoa butter content ranging from about 40% to about 100%, about 50% to about 100%, about 60% to about 100%, about 70% to about 100%, about 80% to about 100%, and about 90% to about 100% by weight of the total fat content of the chocolate. Within the broad range of cocoa butter content (i.e., from about 5% to about 100% by weight of the total fat content), it is contemplated that the lower and/or upper limits of that range may be increased or decreased, respectively, by intervals of about 5%, each such sub-range being contemplated as an embodiment of the invention.

Suitable chocolate may be obtained using any of the various processes known in the art as described in, for example, *The Science of Chocolate*, by Stephen T. Beckett, The Royal Society of London (2000), incorporated by reference in its entirety. The term "chocolate" includes, without limitation, sweet chocolate, semi-sweet chocolate, dark chocolate, milk chocolate, white chocolate, couverture chocolate, baking chocolate, and any of those for which a standard of identity has been established by the U.S. Food and Drug Administration under 21 C.F.R. §163, Subpart B. Of course, it is within the scope of the invention to include other food components commonly found in chocolate confections, such as nut meats, nut butters, puffed grains, fruit, soy, caramel, and the like. Suitable chocolate may be obtained using any of the various processes known in the art as described in, for example, *The Science of Chocolate*, by Stephen T. Beckett, The Royal Society of London (2000), the contents of which are incorporated by reference in its entirety.

In another embodiment, the fat matrix is provided by a so-called "compound coating." The term "compound coating" refers to any cocoa flavored confectionary product wherein some or all of the cocoa butter of chocolate is replaced with a lauric or non-lauric hard butter, such as vegetable fat. Suitable compound coatings are well known in the art and include, for example, those disclosed U.S. Pat. No. 6,251,448 to DeStephen et al., U.S. Pat. No. 5,932,275 to Nalur, and U.S. Pat. No. 4,430,350 to Tresser, the contents of which are incorporated by reference. Other suitable compound coatings are described in Chapter 6 of *Chocolate, Cocoa, and Confectionery: Science and Technology*, by B. W. Minifie, $3^{rd}$ Edition, the contents of which are incorporated by reference.

The amount and type of vegetable fat may be chosen to vary physical properties of the chocolate or compound coating, such as melting point or hardness. For example, if some of the cocoa butter naturally found in the cocoa beans is replaced with a cocoa butter replacer (e.g., a vegetable oil such as palm kernel oil, coconut oil, or soybean oil), the resulting chocolate or compound coating is softer and the melting point is reduced. On the other hand, if some of the cocoa butter is replaced with a cocoa butter equivalent having higher amounts of stearic acid-oleic acid-stearic acid (SOS) moieties than cocoa butter, the melting point is increased. Such techniques of modifying the physical properties of chocolate based on fat eutectics are well known in the art and are discussed in detail in *The Science of Chocolate*, by Stephen T. Beckett, The Royal Society of London, Copyright 2000. A useful melting point range for chocolate according to the present invention is between about 15° C. and about 40° C., more preferably between about 20° C. and about 39° C., even more preferably between about 32° C. and about 38° C., and most preferred between about 32° C. to about 34° C. The melting point of a compound coating may be higher than that of conventional chocolate. The higher melting point of compound coating offers the advantage of stability over a wide range of ambient temperatures. A useful melting point range for chocolate compound coating according to the present invention is between about 33° C. and about 49° C., more preferably between about 35 and about 44° C., even more preferably between about 36° C. and about 38° C.

The physical properties of the chocolate may also be varied by changing the type of cocoa butter that is used or the milk fat content. For example, the melting point of chocolate may be varied by judicious choice of the type of cocoa butter. As a non-limiting example, when Malaysian cocoa butter is used, the resulting chocolate has a higher melting temperature than when Brazilian cocoa butter is used. Alternatively, the melting point of the chocolate can be varied by changing the amount of milk fat. In particular, the melting point of the chocolate may be lowered by increasing the amount of milk fat.

Suitable active agents are not particularly limited and include any substance possessing beneficial biological activity to a human. The active agent may be a liquid or a solid at ambient conditions. Solid active agents may suitably be in the form of a powder. The active agent is dispersed substantially homogeneously throughout the chocolate or compound coating to form a comestible composition with a smooth texture. This may be achieved, for example, by either adding the active agent immediately before or during the conching step of chocolate production, or during a subsequent molding step. When the active agent is in particulate form, it is preferred, but not necessary, to add the active agent during the conching step to ensure that the particles are substantially coated with fat. On the other hand, if the active agent is soluble in melted chocolate, or if the active agent cannot be subjected to physical grinding, the active agent may be blended with the chocolate immediately prior to the molding step. Such is the case for Vitamin $D_3$, for example, because it is normally manufactured with a fragile protective coating that prevents degradation, so that it is not amenable to grinding. If desired, the solubility of the active agent in chocolate may be increased by combining the active agent with an emulsifier prior to it being added to the chocolate.

In a particularly interesting embodiment, the active agent is in particulate form, preferably a powder. In the broadest aspects of the invention, the powder is typically one having a median particle diameter of about 1 to about 25 μm, preferably about 4 to about 15 μm, and more preferably between about 10 and about 13 μm. Surprising results have been obtained with powders having a median particle diameter of about 10 μm to about 13 μm. Specifically included within this range are powders having an average particle size of about 10 μm, about 11 μm, about 12 μm, and about 13 μm. When the average particle size is within the range of about 8 and about 12 μm, it has surprising been found that large amounts of particulate additives may be included without adversely effecting the viscosity of the chocolate melt. In this regard, it has been discovered that chocolate and compound coating may be prepared having 20% by weight or more, 25% by weight or more, and even 30% by weight or more, calcium carbonate powder having an average particle size between about 10 µm to about 13 µm. The resulting products have a texture and mouthfeel comparable to chocolate or compound coating to which calcium carbonate powder has not been added.

In other exemplary embodiments, the powder has a median particle size of about 2 µm, about 4 µm, about 6 µm, about 8 µm, about 10 µm, about 12 µm, about 15 µm, or about 20 µm. The particle size distribution is typically broad. In one embodiment, the particle size distribution has a full-width at half maximum (FWHM) that is at least about 5% of the median particle size, preferably at least about 15% of the median particle size, more preferably at least about 25% of the median particle size, and even more preferably, at least about 50% of the median particle size. In one interesting embodiment, the median particle size of the active agent is about 12 µm and the FWHM of the particle distribution is about 5 µm.

The micron-sized powder comprising the active agent may be produced by physical comminution of an active agent to a desired median particle size and/or particle size distribution by physical grinding, milling and the like. Methods are known in the art for producing fine powders, non-limiting examples of which include granulating, hammer milling, jet milling, ball milling, media milling or grinding by using a mortar and pestle. It is within the ordinary skill in the art to provide powders of active agents having any desired median particle size and particle size distribution.

In other embodiments, active agents which themselves are not in particulate form may be converted to particulate form before incorporation into the fat matrix. Powders of active agent may be obtained, for example, by applying an active agent to a pharmaceutically inert particle support, such as lactose, cellulose, silica and the like. This approach may be desirable, for example, where the required amount of active agent is so small that it becomes difficult to handle or to measure accurately. By applying the active agent to a particle support, the active agent becomes spread over a greater amount of material, so that conventional sample handling or measurement methods can be employed without sacrificing a substantial portion of the active agent. Suitably, the active agent is dissolved or suspended in a pharmaceutically acceptable liquid or is itself a liquid. The active agent may be applied to the particle support by any of the methods known in the art for coating powders, including spray coating or fluidized bed coating. To promote adhesion of the active agent to the particle support, the pharmaceutically acceptable liquid optionally may contain an adhesion agent. The adhesion agent may be, for example, a pharmaceutically acceptable polymer that helps to entrap the active agent on the surface of the particle support during the powder coating process or after the liquid has evaporated. Alternatively, the active agent may be microencapsulated with a shell material. Techniques for producing microencapsulated materials are well know in the art. Powders comprising microencapsulated active agents or active agents dispersed on a particulate support will have the same median particle size and particle size distribution described above.

One aspect of this invention is the recognition that it is advantageous to control the particle size range of the particulate active agent in order to obtain high levels of incorporation of the active agent without having deleterious effects on the texture and organoleptic properties of the chocolate or compound coating composition. Without wishing to be bound by any theory, it is believed that when the median particle size of a particulate active agent is very small (e.g., below about 10 microns), the total surface area of the active agent becomes very large, according to the well known relationship between particle size and surface area. When this happens, the particulate active agent may not be sufficiently coated by the limited amount of fat in the chocolate, resulting in inadequate incorporation of the active agent into the chocolate and/or increase in the viscosity of the chocolate or compound coating. On the other hand, when the median particle size of the active agent is greater than about 15 µm the chocolate or compound coating is perceived as being overly gritty and lacking the smooth texture normally associated with chocolate and compound coating. The finding that powders having a median particle diameter of about 10-13 µm can be formulated into chocolate and compound coatings at high levels is particularly surprising in light of conventional wisdom which dictates that it is necessary to provide active agents in the sub-micron range. See e.g. U.S. Pat. No. 4,609,543, which is incorporated by reference in its entirety.

Another aspect of the invention is therefore to provide high levels of incorporation of a powder into a fat matrix, such as chocolate or chocolate compound coating, without deleterious effects on the viscosity of melted or liquid matrix. Without wishing to be bound by any particular theory, it is believed that the viscosity of melted or liquid chocolate will depend, at least in part, on both the particle size and particle size distribution of the powder. Small particles present a greater surface area to be solvated by fat. Thus a very large surface area of a bulk powder can disrupt the packing of fat molecules due to the ordering required to fully solvate the powder. Further, when the particle size distribution of the particulate active agent is very narrow, the packing of the active agent particles in the fat matrix is inefficient, limiting the amount of active agent which can be incorporated in the chocolate or compound coating. By providing a powder with a broad particle size distribution, tighter packing of the powder is possible and thus less fat is required to solvate small clusters of active agent on a weight basis.

The apparent viscosity of the melted fat matrix, including chocolate or chocolate compound coating, should be within a range suitable for forming solid bars when cooled to room temperature. Typically, the apparent viscosity of the melt will be within ±50%, preferably ±25%, more preferably ±10%, and more preferred still ±5% of the apparent viscosity of comparable fat matrix to which the particulate agent has not been added. In some embodiments, the melted chocolate or chocolate compound coating will have an apparent viscosity of about 500 to about 200,000 cP (centipoises), about 1,000 to about 100,000 cP, about 5,000 to about 50,000 cP, about 10,000 to about 40,000 cP, or about 15,000 to about 30,000 cP at 50° C. and a spindle rate of 20 RPM. Typically, although not necessarily, the apparent viscosity of chocolate or chocolate compound coating in the absence of particulate additives such as calcium carbonate powder will be about 10,000 to about 30,000 cP, and more typically about 25,000 cP, as measured on a Brookfield viscometer model DV-11+ using an LV1 spindle operating at 20 RPM at about 56° C. It will be recognized however, that due to the large differences in viscosity among the various types of chocolate and chocolate compound coating, these values are merely illustrative and are not representative of all chocolate and chocolate compound coating, or other fat matrices, within the scope of the invention.

In certain embodiments of the invention, the active agent is a nutraceutical, such as a vitamin or a substance derived from a plant or animal source. Non-limiting examples of suitable agents include vitamins A, $B_6$, $B_{12}$, C, D, E, K, thiamin, riboflavin, niacin, folic acid, biotin, pantothenic acid, calcium, phosphorus, iodine, magnesium, zinc, selenium, copper, manganese, chromium, molybdenum, chloride, potassium, boron, nickel, silicon, and vanadium. Nutraceuticals derived from plants or animals may include, without limitation, aloe, bilberry, black cohash, chamomile, chasteberry tree, chondroitin, co-enzyme Q10, dong quai, echinacea, evening primrose oil, feverfew, garlic, ginger, gingko biloba, ginseng, glucosamine, green tea, guarana, hawthorn, horse chestnut, isoflavones, kava-kava, lutein, lycopene, milk thistle, nettle, omega-3 fatty acids, sam-e, St. John's wort, docosahexaenoic acid (DHA) and eicosapentaenoic acid (EPA), saw palmetto, tea tree oil, valerian, and yohimbe, and the like.

Calcium carbonate is a currently preferred active agent according to the invention. It is well known in the art that calcium carbonate powders having a variety of median particle diameters are commercially available. For example, food grade and USP grade calcium carbonate powders having median particle diameters ranging from 0.7 to 20 µm are available from suppliers such as Omya, Inc. (Alpharetta, Ga.), Omya Arizona, Inc. (Lucerne Valley, Calif.), J. M Huber Corp. (Atlanta, Ga.), and Minerals Technologies Inc. (New York, N.Y.). Suitable calcium carbonate powders having a median particle size of 15 µm, in some embodiments, may be characterized by a distribution where about 65% or more of the bulk volume of the powder has a particle size between 5 and 25 µm (±66% from the median) and about 40% or more of the bulk volume has a particle size between about 10 and 20 µm (±33% from the median). Similarly, suitable calcium carbonate powders having a median particle size of 12 µm, according to one embodiment, may be characterized by a distribution where about 50% or more of the bulk volume of the powder has a particle size between 4 and 20 µm (±66% from the median) and about 30% or more of the bulk volume has a particle size between about 8 and 16 µm (±33% from the median). Suitable calcium carbonate powders having a median particle size of 6 µm, according to one embodiment, may be characterized by a distribution where about 55% or more of the bulk volume of the powder has a particle size between 2 and 10 µm (±66% from the median) and about 25% or more of the bulk volume has a particle size between about 4 and 8 µm (±33% from the median). Suitable calcium carbonate powders having a median particle size of 3-4 µm, according to one embodiment, may be characterized by a distribution where about 50% or more of the bulk volume of the powder has a particle size between 1.2 and 5.8 µm (±66% from the median) and about 25% or more of the bulk volume has a particle size between about 2.3 and 4.7 µm (±33% from the median). Suitable calcium carbonate powders include, but are not limited to those available from OMYA, Inc. under the tradenames OMYA-Cal FG 15, OMYA-Cal USP 15, OMYA-Cal LL OC FG 15 BTH, OMYA-Cal LL USP 15, OMYA-Cal LL USP 15 BTH, OMYA-Cal FG-10AZ, OMYA-Cal FG-6AZ, and OMYA-Cal USP-4AZ.

In other embodiments of the invention, the active agent or particulate active agent is a pharmaceutical. Non-limiting examples of suitable pharmaceuticals include anti-infectives such as antibiotics and antiviral agents; analgesics and analgesic combinations; local and general anesthetics; anorexics; antiarthritics; antiasthmatic agents; anticonvulsants; antidepressants; antihistamines; anti-inflammatory agents; antinauseants; antineoplastics; antipruritics; antipsychotics; antipyretics; antispasmodics; birth control preparations; cardiovascular preparations (including calcium channel blockers, beta-blockers, beta-agonists and antiarrythmics); antihypertensives; diuretics; vasodilators; central nervous system stimulants; cough and cold preparations; decongestants; diagnostics; hormones; bone growth stimulants and bone resorption inhibitors; immunosuppressives; muscle relaxants; psychostimulants; sedatives; tranquilizers; proteins, peptides and fragments thereof, and the like.

Typically, particulate active agents will be incorporated into chocolate or compound coating at levels between about 0.5% to about 50% on a weight basis. More typically, the active agent will comprise about 1 to about 30% by weight of the chocolate or compound coating. By practicing the methods of this invention, it is possible to obtain active agent-containing chocolate or compound coating confections with a smooth texture, even if relatively large amounts of active agent are present, for example 20% by weight or more, 25% by weight or more, and even 30% by weight or more. By way of example, a piece of chocolate having a total weight of about 7 grams will typically, though not necessarily, contain from about 1 mg to about 1,800 mg of active agents.

EXAMPLE 1

The effect of calcium carbonate particle size on the properties of chocolate compound coating was examined.

Samples A-D were prepared by blending the calcium carbonate powders shown in FIG. 2 with melted dark compound chocolate (Peters, 33% cocoa butter and butter fat) at a weight ratio of calcium carbonate to compound chocolate of 1:3.4. The melted compound chocolate/calcium carbonate mixture was conched and allowed to solidify. The solid mixture was remelted and Vitamin $D_3$ was blended in at a weight ratio of about 1:13 Vitamin $D_3$ to chocolate compound/calcium carbonate mixture. The melted chocolate compound mixtures containing calcium carbonate and Vitamin $D_3$ were molded to form chocolate bars having a weight of 7 grams. The chocolate bars nominally contained about 5.1 grams of chocolate, about 1.5 grams of calcium carbonate powder, and about 400 mg of Vitamin $D_3$.

The chocolate bars corresponding to each of the different size calcium carbonate powders (samples A-D) were visually inspected by examining the outside surface of each bar and a cross section of the bar to assess the homogeneity of the product. The bars were also tasted to determine the effects of the calcium carbonate and/or Vitamin $D_3$ on the organoleptic properties of the chocolate compound coating. The results are summarized in Table 2.

TABLE 2

EFFECT OF PARTICLE SIZE ON CALCIUM-FORTIFIED CHOCOLATE COMPOUND COATING

| Sample | Calcium carbonate | Median Diameter | Observations |
|---|---|---|---|
| A | OMYA-CAL FG-4 AZ | 4 µm | Pasty texture/chalky taste Inhomogeneous |
| B | OMYA-CAL FG-6 AZ | 6 µm | Pasty texture/chalky taste Inhomogeneous |
| C | OMYA-CAL FG-10 AZ | 12 µm | Smooth/normal chocolate homogeneous |
| D | OMYA-CAL FG-15 AZ | 15 µm | Pasty texture/chalky taste Inhomogeneous |

Visual inspection revealed that the calcium carbonate powders having median particle diameters of 4, 6, and 15 microns (samples A, B, and D) did not blend homogeneously with the chocolate compound coating. Regions of localized calcium carbonate powder inhomogeneity were clearly visible on the surface and interior of the chocolate bars. Samples A, B, and D were described as having a "chalky" taste and a "pasty" mouthfeel not normally associated with chocolate or chocolate compound coating. In contrast, sample C, comprising 12 micron median particle diameter calcium carbonate powder, yielded a homogeneous bar with no indication of localized clumping of calcium carbonate powder. Moreover, the chocolate bar had a mouthfeel and taste substantially identical to that of a normal (i.e., unfortified) chocolate compound coating.

EXAMPLE 2

The effect of mixing two calcium carbonate powders of differing particle size on the properties of chocolate compound coating was examined, as shown in Table 3.

TABLE 3

MIXTURES OF CALCIUM CARBONATE POWDERS OF DIFFERENT MEDIAN DIAMETERS

| Sample | Calcium carbonate | Median Diameter | Observations |
|---|---|---|---|
| A (Example 1) | OMYA-CAL FG-4 AZ | 4 μm | Pasty texture/ chalky taste Inhomogeneous |
| D (Example 1) | OMYA-CAL FG-15 AZ | 15 μm | Pasty texture/ chalky taste Inhomogeneous |
| E | OMYA-CAL FG-4 AZ (1 part) + OMYA-CAL FG-15 AZ (1.5 parts) | ~11 μm | Smooth/ normal chocolate homogeneous |

Sample E was prepared by blending one part OMYA-CAL FG-4 AZ calcium carbonate powder (4 μm median particle diameter) and 1.5 parts OMYA-CAL FG-15 AZ calcium carbonate powder (15 μm median particle diameter) with melted dark compound chocolate (Peters, 33% cocoa butter and butter fat) at a weight ratio of 1:1.5:8.5 (OMYA-CAL FG-4 AZ/OMYA-CAL FG-15 AZ/chocolate compound coating). The total weight ratio of calcium carbonate to chocolate compound coating was 1:3.4, as in Example 1. The mixture was conched and allowed to solidify. After solidification, the mixture was remelted and combined with Vitamin $D_3$ at a weight ratio of 1:12.75 (Vitamin $D_3$ to chocolate compound coating/calcium carbonate mixture). A sample of the mixture was molded to form a 7 gram chocolate bar that nominally contained about 0.6 grams of OMYA-CAL FG-4 AZ, about 0.9 grams of OMYA-CAL FG-15 AZ, about 400 mg of Vitamin $D_3$, and about 5.1 grams of chocolate compound coating.

As in Example 1, the outside surface and cross section of the resulting calcium-fortified chocolate bar (Sample E) was visually inspected and the chocolate bar was tasted. Surprisingly, unlike the case where the OMYA-CAL FG-4 AZ and OMYA-CAL FG-15 AZ powders were added alone, the addition of both powders to the melted chocolate resulted in a chocolate bar that had a homogeneous dispersion of calcium carbonate and a taste and texture substantially identical to normal, unfortified chocolate compound coating. It will be observed that the combination of one part OMYA-CAL FG-4 AZ calcium carbonate powder having a 4 μm median particle diameter and 1.5 parts OMYA-CAL FG-15 AZ calcium carbonate powder having a 15 μm median particle diameter yields a powder having a median particle diameter of about 11 ∞m. The results obtained with the 11 μm powder were substantially identical to the results obtained with the 12 μm powder (Sample C) of Example 1. It is believed that the 4 μm and 15 μm powder could, in the alternative, first be mixed together and subsequently added to the chocolate compound coating with identical results.

EXAMPLE 3

Chocolate Multivitamin

The multivitamin components listed in Table 4 were blended into melted dark compound chocolate (Peters, 33% cocoa butter and butter fat), which was subsequently solidified to form a chocolate bar weighing 7 grams. The quantity of each component shown in Table 4 were chosen to be the amounts found in a commercially available Centrum Silver™ multivitamin. The calcium carbonate was OMYA-CAL FG-10 AZ having a median particle diameter of 12 μm.

TABLE 4

CHOCOLATE MULTIVITAMIN

| Active Agent | Amount | Source |
|---|---|---|
| Vitamin A | 3500 IU | Vitamin A acetate, Beta-carotene |
| Vitamin C | 60 mg | Sodium Ascorbate |
| Vitamin D | 400 IU | Ergocalciferol |
| Vitamin E | 45 IU | D,L-alpha tocopheryl acetate |
| Vitamin K | 10 mcg | Phytonadione |
| Thiamin | 1.5 mg | Thiamin Mononitrate |
| Riboflavin | 1.7 mg | Riboflavin |
| Niacin | 20 mg | Niacinamide |
| Vitamin $B_6$ | 3 mg | Pyrodoxine Hydrochloride |
| Folic Acid | 400 mcg | Folic Acid |
| Vitamin $B_{12}$ | 25 mcg | Cyanocobalamin |
| Biotin | 30 mcg | Biotin |
| Pantothenic Acid | 10 mg | Calcium Pantothenate |
| Calcium | 200 mg | Calcium Carbonate |
| Phosphorus | 48 mg | Calcium Phosphate Dibasic |
| Iodine | 150 mcg | Potassium Iodide |
| Magnesium | 100 mg | Magnesium oxide |
| Zinc | 15 mg | Zinc oxide |
| Selenium | 20 mcg | Sodium selenate |
| Copper | 2 mg | Cupric oxide |
| Manganese | 2 mg | Maganese sulfate |
| Chromium | 150 mcg | Chromium chloride |
| Molybdenum | 75 mcg | Sodium molybdate |
| Chloride | 72 mg | Potassium chloride |
| Potassium | 80 mg | Potassium iodide/Potassium chloride |
| Boron | 150 mcg | Sodium borate |
| Nickel | 5 mcg | Nickel sulfate |
| Silicon | 2 mg | Silicon dioxide/silicon metasilicate |
| Vanadium | 10 mcg | Sodium metavanadate |
| Lutein | 250 mcg | Lutein |
| Lycopene | 300 mcg | lycopene |

The outside surface and cross section of the chocolate bar was visually inspected and the chocolate bar was tasted. Despite the presence of the different components in Table 4, the resulting chocolate bar appeared homogeneous without localized concentrations of solid components and had a taste and texture substantially identical to normal, unfortified chocolate compound coating. The chocolate compound coating effectively masked the taste of the vitamin and mineral components.

In some embodiments of the invention, a dietary supplement may comprise one or more of the active agents listed in Table 4.

EXAMPLE 4

The effect of calcium carbonate particle size on the viscosity of melted semi-sweet dark chocolate was investigated. For this Example, the samples were prepared by melting 330 g of chocolate at approximately 56° C. using a water bath. 90 g of calcium carbonate powder was stirred into the chocolate until uniform. The resulting samples contained about 21% by weight calcium carbonate based on the total weight of the composition.

Sample 1 was prepared with calcium carbonate powder having and average particle diameter of about 12 µm; Sample 2 was prepared with calcium carbonate powder having and average particle diameter of about 0.8 µm; and Sample 3 was prepared with calcium carbonate powder having and average particle size of 0.07 µm. Sample 3 was selected to be representative of the compositions described in U.S. Pat. No. 4,609,543, the contents of which are incorporated by reference.

The viscosity of the melted samples was measured on a Brookfield viscometer model DV-11+ using the LV1 spindle (operating range of 15 to 6,000,000 cP) at temperatures ranging from about 35° C. to about 54.5° C.

The apparent viscosity measurements for Samples 1 and 2 are shown in Table 5.

TABLE 5

| Sample 1 20 RPM Spindle Rate | | Sample 2 2 RPM Spindle Rate | |
|---|---|---|---|
| Temperature (° C.) | Viscosity (cP) | Temperature (° C.) | Viscosity (cP) |
| 54.5 | 18,800 | 54.6 | 210,000 |
| 49.4 | 19,600 | 50.3 | 215,000 |
| 45.5 | 21,000 | 45.5 | 220,000 |
| 40.7 | 22,700 | 40.1 | 230,000 |
| 35.0 | 27,500 | 35.0 | 245,000 |

Sample 1 was found to have an ideal viscosity for forming molding bars. Bars formed from chocolate comprising 21 weight % of 12 µm calcium carbonate have a texture substantially identical to chocolate prepared without calcium carbonate added. In contrast, the viscosity of Sample 2 was too high to form molded bars. It should be noted that the viscosity measurements for Sample 2 could not be determined at a spindle rate of 20 RPM and instead were determined using a spindle rate of 2 RPM, due to the very high viscosity of the material. Chocolate and chocolate compound coating are non-Newtonian fluids and therefore the apparent viscosity increases with shear force. As will be evident to the skilled artisan, the apparent viscosity of Sample 2 would be much higher at 20 RPM.

It was not possible to measure the viscosity of Sample 3 because it was far above the viscosity limits of the viscometer. Even at very low shear, i.e., about 1 RPM, the apparent viscosity was estimated to be above 6 million cP. Upon cooling, the compound coating did not solidify into a form suitable for preparing molded bars but rather had the consistency of a soft, sticky, semi-solid.

The invention having been described by the foregoing description of the preferred embodiments, it will be understood that the skilled artisan may make modifications and variations of these embodiments without departing from the spirit or scope of the invention as set forth in the following claims.

The invention claimed is:

1. A method for preparing a dietary supplement comprising:
   (1) providing chocolate or chocolate compound coating; said chocolate or chocolate compound coating comprising cocoa butter;
   (2) providing calcium carbonate powder having a median particle size between about 1 µm and about 25 µm;
   (3) conching said calcium carbonate powder with said chocolate or chocolate compound coating to coat the particles of calcium carbonate with cocoa butter wherein said calcium carbonate powder is present in an amount sufficient to provide a dietary supplement having at least about 10% calcium carbonate powder by weight;
   (4) providing an active agent microencapsulated in a shell material;
   (5) dispersing said microencapsulated active agent in molten chocolate or chocolate compound coating subsequent to said conching step;
   thereby providing chocolate or chocolate compound coating comprising calcium carbonate powder and an active agent homogenously dispersed throughout said chocolate or chocolate compound coating and having a melting point between about 30° C. and about 49° C. and an apparent viscosity, in the molten state, within about ±50% of the apparent viscosity of the identical chocolate or chocolate compound coating in the absence of the calcium carbonate powder, as measured under conditions of identical temperature and shear.

2. The method of claim 1 wherein said calcium carbonate powder has a median particle size between about 4 µm and about 15 µm.

3. The method of claim 2 wherein said calcium carbonate powder has a median particle size of about 4 µm.

4. The method of claim 3 wherein said calcium carbonate powder having a median particle size of about 4 µm is characterized by a particle size distribution where about 50% or more of the bulk volume of the powder has a particle size between 1.2 and 5.8 µm and about 25% or more of the bulk volume has a particle size between about 2.3 and 4.7 µm.

5. The method of claim 2 wherein said calcium carbonate powder has a median particle size between about 10 µm and about 13 µm.

6. The method of claim 1, wherein said apparent viscosity in the molten state is within about ±25% of the apparent viscosity of the identical chocolate or chocolate compound coating in the absence of the calcium carbonate powder, as measured under conditions of identical temperature and shear.

7. The method of claim 1, wherein said apparent viscosity in the molten state is within about ±10% of the apparent viscosity of the identical chocolate or chocolate compound coating in the absence of the calcium carbonate powder, as measured under conditions of identical temperature and shear.

8. The method of claim 1, wherein said apparent viscosity in the molten state within about ±5% of the apparent viscosity of the identical chocolate or chocolate compound coating in the absence of the calcium carbonate powder, as measured under conditions of identical temperature and shear.

9. The method of claim 1 wherein said calcium carbonate powder comprises at least about 20% by weight of said dietary supplement.

10. The method of claim 1 wherein said calcium carbonate powder comprises at least about 25% by weight of said dietary supplement.

11. The method of claim 1 wherein said calcium carbonate powder comprises at least about 30% by weight of said dietary supplement.

12. The method of claim 1 wherein said microencapsulated active agent has a median particle size between about 1 µm and about 25 µm.

13. A method for preparing a dietary supplement comprising:
(1) providing chocolate or chocolate compound coating, said chocolate or chocolate compound coating comprising cocoa butter;
(2) providing calcium carbonate powder having a median particle size between about 1 μm and about 25 μm;
(3) conching said calcium carbonate powder with said chocolate or chocolate compound coating to coat the particles of calcium carbonate with cocoa butter, wherein said calcium carbonate powder is present in an amount sufficient to provide a dietary supplement having at least about 10% calcium carbonate powder by weight;
(4) adding vitamin D and vitamin K to molten chocolate or chocolate compound coating after the conching step but prior to molding; and
(5) molding said mixture;
thereby providing a dietary supplement comprising calcium carbonate powder homogenously dispersed throughout said chocolate or chocolate compound coating and having a melting point between about 30° C. and about 49° C. and an apparent viscosity, in the molten state, within about ±50% of the apparent viscosity of the identical chocolate or chocolate compound coating in the absence of the calcium carbonate powder, as measured under conditions of identical temperature and shear.

14. The method of claim 13 wherein said calcium carbonate powder has a median particle size between about 4 μm and about 15 μm.

15. The method of claim 14 wherein said calcium carbonate powder has a median particle size of about 4 μm.

16. The method of claim 15 wherein said calcium carbonate powder having a median particle size of about 4 μm is characterized by a particle size distribution where about 50% or more of the bulk volume of the powder has a particle size between 1.2 and 5.8 μm and about 25% or more of the bulk volume has a particle size between about 2.3 and 4.7 μm.

17. The method of claim 14 wherein said calcium carbonate powder has a median particle size between about 10 μm and about 13 μm.

18. The method of claim 13, wherein said apparent viscosity in the molten state is within about +25% of the apparent viscosity of the identical chocolate or chocolate compound coating in the absence of the calcium carbonate powder, as measured under conditions of identical temperature and shear.

19. The method of claim 13, wherein said apparent viscosity in the molten state is Within about ±10% of the apparent viscosity of the identical chocolate or chocolate compound coating in the absence of the calcium carbonate powder, as measured under conditions of identical temperature and shear.

20. The method of claim 13, wherein said apparent viscosity in the molten state within about ±5% of the apparent viscosity of the identical chocolate or chocolate compound coating in the absence of the calcium carbonate powder, as measured under conditions of identical temperature and shear.

21. The method of claim 13 wherein said dietary supplement comprises at least about 20% of the calcium carbonate powder.

22. The method of claim 13 wherein said dietary supplement comprises at least about 25% of the calcium carbonate powder.

23. The method of claim 13 wherein said dietary supplement comprises at least about 30% of the calcium carbonate powder.

24. A method for preparing a dietary supplement comprising:
conching calcium carbonate powder having a median particle size between about 1 μm and about 25 μm with a chocolate or chocolate compound coating comprising cocoa butter and, optionally thereafter adding one or more active agents to the molten chocolate or chocolate compound coating comprising cocoa butter, the calcium carbonate being present in an amount sufficient to provide a dietary supplement comprising at least about 10% by weight calcium carbonate:, the chocolate or chocolate compound coating comprising cocoa butter having a melting point between about 30° C. and about 49° C. and an apparent viscosity, in the molten state, within about ±50% of the apparent viscosity of the identical chocolate or chocolate compound coating comprising cocoa butter in the absence of the calcium carbonate powder, as measured under conditions of identical temperature and shear.

25. The method of claim 24 wherein said calcium carbonate powder has a median particle size of about 4 μm.

26. The method of claim 24 wherein said calcium carbonate powder having a median particle size of about 4 μm is characterized by a particle size distribution wherein about 50% or more of the bulk volume of the powder has a particle size between 1.2 and 5.8 μm and about 25% or more of the bulk volume has a particle size between about 2.3 and 4.7 μm.

27. The method of claim 24 wherein said calcium carbonate powder has a median particle size between about 10 μm and about 13 μm.

28. The method of claim 24 wherein said cocoa butter solidifies into the Form V polymorphic crystalline form at room temperature.

29. The method of claim 24 wherein said one or more active agents includes vitamin D.

30. The method of claim 24 wherein said vitamin D is microencapsulated in a shell material.

31. The method of claim 24 wherein said one or more active agents include vitamin D and vitamin K.

32. A method for preparing a dietary supplement comprising:
(1) providing chocolate; said chocolate comprising cocoa butter; said cocoa butter comprising from about 5% to about 100% of the total fat of said chocolate;
(2) providing calcium carbonate powder having a median particle size of about 4 μm;
(3) conching said calcium carbonate powder with said chocolate to coat the particles of calcium carbonate with fat, wherein said calcium carbonate powder is present in an amount sufficient to provide a dietary supplement having at least about 10% calcium carbonate powder by weight;

(4) providing vitamin D microencapsulated in a shell material;
(5) dispersing said microencapsulated vitamin D in molten chocolate subsequent to said conching step;
(6) solidifying said chocolate in the Form V polymorphic crystalline form;
thereby providing chocolate comprising calcium carbonate powder and vitamin D homogenously dispersed throughout said chocolate and having a melting point below mouth temperature and an apparent viscosity, in the molten state, within about ±50% of the apparent viscosity of the identical chocolate in the absence of the calcium carbonate powder, as measured under conditions of identical temperature and shear.

* * * * *

UNITED STATES PATENT AND TRADEMARK OFFICE
CERTIFICATE OF CORRECTION

| | | |
|---|---|---|
| PATENT NO. | : 7,931,930 B2 | Page 1 of 1 |
| APPLICATION NO. | : 11/561294 | |
| DATED | : April 26, 2011 | |
| INVENTOR(S) | : Lang et al. | |

It is certified that error appears in the above-identified patent and that said Letters Patent is hereby corrected as shown below:

In the Claims

Column 15, line 49, delete "about +25%" and insert -- about ±25% --

Column 15, line 56, delete "Within" and insert -- within --

Column 16, line 22, delete "carbonate:," and insert -- carbonate; --

Signed and Sealed this
Twenty-eighth Day of April, 2015

Michelle K. Lee
*Director of the United States Patent and Trademark Office*